United States Patent [19]

Ludwig

[11] Patent Number: 5,271,592
[45] Date of Patent: Dec. 21, 1993

[54] THREE-DIMENSIONAL ADJUSTABLE CEILING SUSPENSION FOR A SURGICAL MICROSCOPE

[75] Inventor: Manfred Ludwig, Jena, Fed. Rep. of Germany

[73] Assignee: Carl Zeiss Jena GmbH, Jena, Fed. Rep. of Germany

[21] Appl. No.: 936,320

[22] Filed: Aug. 28, 1992

[30] Foreign Application Priority Data

Aug. 29, 1991 [DE] Fed. Rep. of Germany ....... 4128669

[51] Int. Cl.⁵ ............................................. B42F 13/00
[52] U.S. Cl. .................................. 248/333; 248/343; 359/384
[58] Field of Search ............... 248/333, 317, 326, 343; 359/384, 429

[56] References Cited

U.S. PATENT DOCUMENTS

3,887,267  6/1975  Heller ................................. 359/384
4,815,832  3/1989  Nagano et al. ...................... 359/384

OTHER PUBLICATIONS

"Zeiss OPS 351 OPM 250 F/251 F, Operationsmikroskop am Deckenstativ", Carl Zeiss Jena, No. 60-143-1, Germany.

*Primary Examiner*—Ramon O. Ramirez
*Attorney, Agent, or Firm*—Walter Ottesen

[57] ABSTRACT

A three-dimensional adjustable ceiling suspension for a surgical microscope includes a first platform for holding the surgical microscope and a second platform connected to a ceiling disposed above and in spaced relationship to the first platform. Six extendable connecting elements interconnect the two platforms. Six lower articulating joints connect the connecting elements to the first platform and six upper articulating joints connect the connecting elements to the second platform. The lower articulating joints are disposed on the first platform along an imaginary first circle and the upper articulating joints are disposed on the second platform along an imaginary second circle. A plurality of drive units are connected to corresponding ones of the extendable connecting elements. A computer-supported drive makes it possible to freely select the position of the surgical microscope as well as realize a rotation and inclination about an imaginary fixed point lying in the center of the object field. The position control of the surgical microscope takes place via a coordinate drive of the longitudinally extendable connecting elements between the two platforms.

4 Claims, 3 Drawing Sheets

THREE-DIMENSIONAL ADJUSTABLE CEILING SUSPENSION FOR A SURGICAL MICROSCOPE

BACKGROUND OF THE INVENTION

Ceiling suspensions for surgical microscopes are disclosed, for example, in the Zeiss publication entitled "Zeiss OPM 250F, 251F", brochure number 60-143-1. These ceiling suspensions have a configuration which includes a column suspended perpendicularly from the ceiling and a support arm pivotally mounted at right angles as well as a parallelogram arm pivotally connected for mounting the microscope. With this assembly, further degrees of freedom or rotation and inclination can be realized.

The arrangement has the following disadvantages. The ceiling of the operating room on which the support is suspended must have an especially high rigidity in order to prevent vibrations which can be transmitted to the support. The structural measures and requirements are complex especially for a subsequent installation in an operating room.

The L-shaped construction of the support column with the carrier arm and the parallelogram arm is very unfavorable with respect to vibration behavior and requires a correspondingly strong design for the swivel joint as well as for the column, support arm and parallelogram arm. The microscope can only be positioned in a circularly-shaped region around the central column; that is, the largest portion of the region of movement is practically unuseable and the most favorable case with respect to vibration for the position below the suspension is not realizable because of geometric reasons.

Arrangements for variably counterbalancing weight for the application of various configurations of the microscope and accessories of different weights complicate the structural configuration of the parallelogram arm.

The elevation to which the column extends downwardly is determined by the compromise between the mutually opposing requirements of floor clearance and comfortable operability of the operator-actuable elements mounted on the column and this compromise cannot be optimally configured because of the different body sizes of individual operators of the equipment.

SUMMARY OF THE INVENTION

It is an object of the invention to provide a ceiling suspension for a surgical microscope which provides all required degrees of freedom for mounting the surgical microscope head while at the same time providing a high static and dynamic stability. The stability is obtained with substantially reduced structural requirements. The primary operating position is at the same time the position having the highest stability with respect to vibrations. Additional elements for providing weight counterbalance are no longer necessary.

The ceiling suspension makes possible the integration of a sterile covering of the microscope as well as ancillary equipment such as positioning aids and illuminating devices.

A pivoting movement out of the region above the operating area is possible such that no impediments occur.

The return pivoting movement into the work position takes place exactly in the previously adjusted position.

With the invention, a computer-supported drive makes it possible to freely select the position of the surgical microscope as well as realize a rotation and inclination about an imaginary fixed point lying in the center of the object field. The position control of the surgical microscope takes place via a coordinate drive of the longitudinally extendable connecting elements between the two platforms.

BRIEF DESCRIPTION OF THE DRAWINGS

The invention will now be described with reference to the drawings wherein.

DESCRIPTION OF THE PREFERRED EMBODIMENTS OF THE INVENTION

Figures 1, 1A:
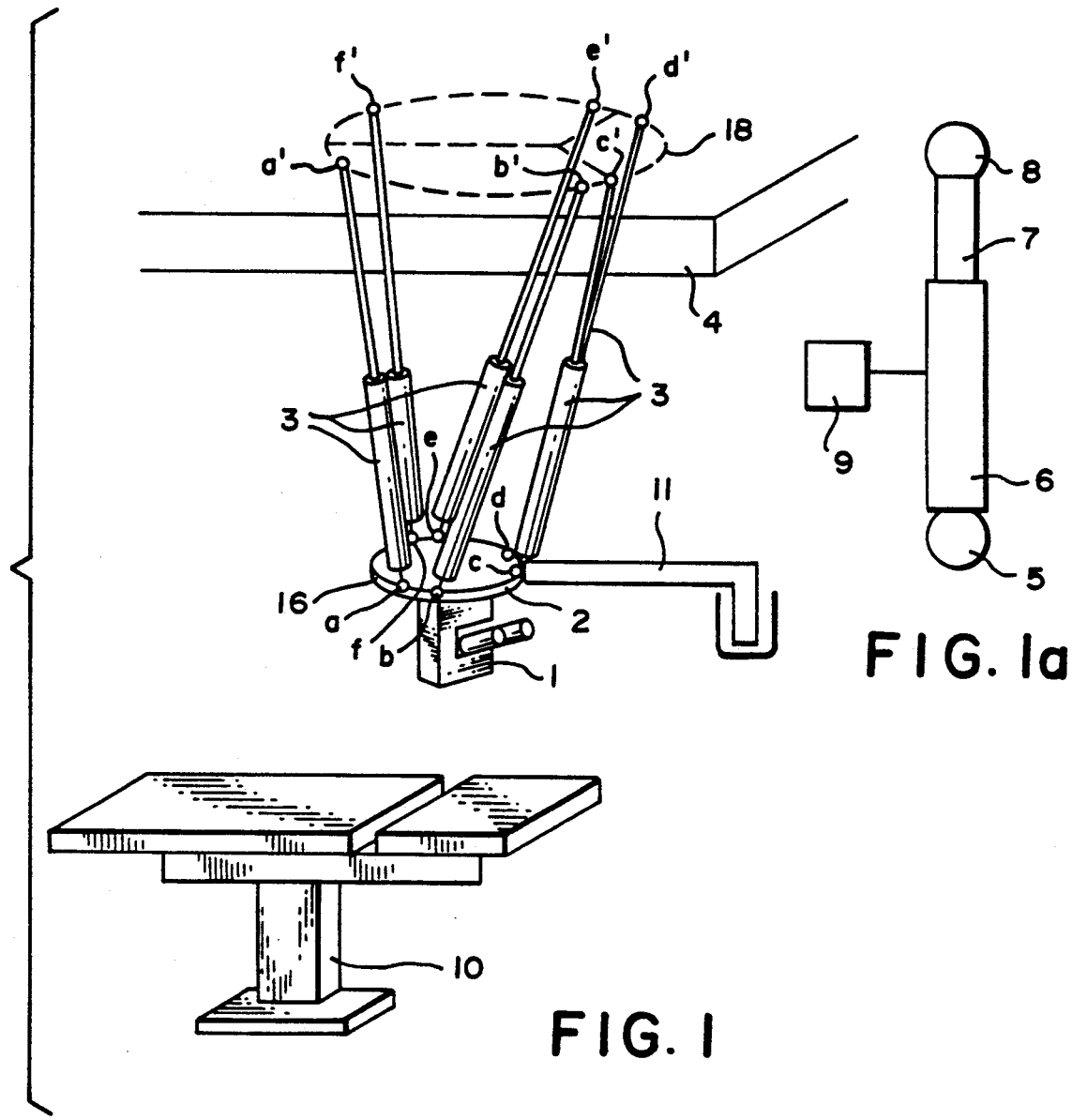
FIG. 1 is an embodiment of the ceiling suspension of the invention for surgical microscopes.
FIG. 1a is a schematic representation of one of the extendable connecting elements.

A surgical microscope 1 above the primary operating area of an operating table 10 is attached to a platform 2 which is connected via six connecting elements 3 to a further platform 4 attached to the ceiling of the operating room. The connecting elements 3 are connected to the platforms 2 and 4 via ball joints.

The possible configuration of the longitudinally adjustable connecting elements 3 is shown in FIG. 1a. Ball joints are identified by reference numerals 5 and 8 and the connecting element 3 comprises the sleeve 6 in which a rod 7 is displaceably mounted.

The length adjustment of the elements 3 takes place, for example, in analogy to the principle of a hydraulic cylinder or by means of an electrically driven spindle drive or via a linear motor.

Figure 3:
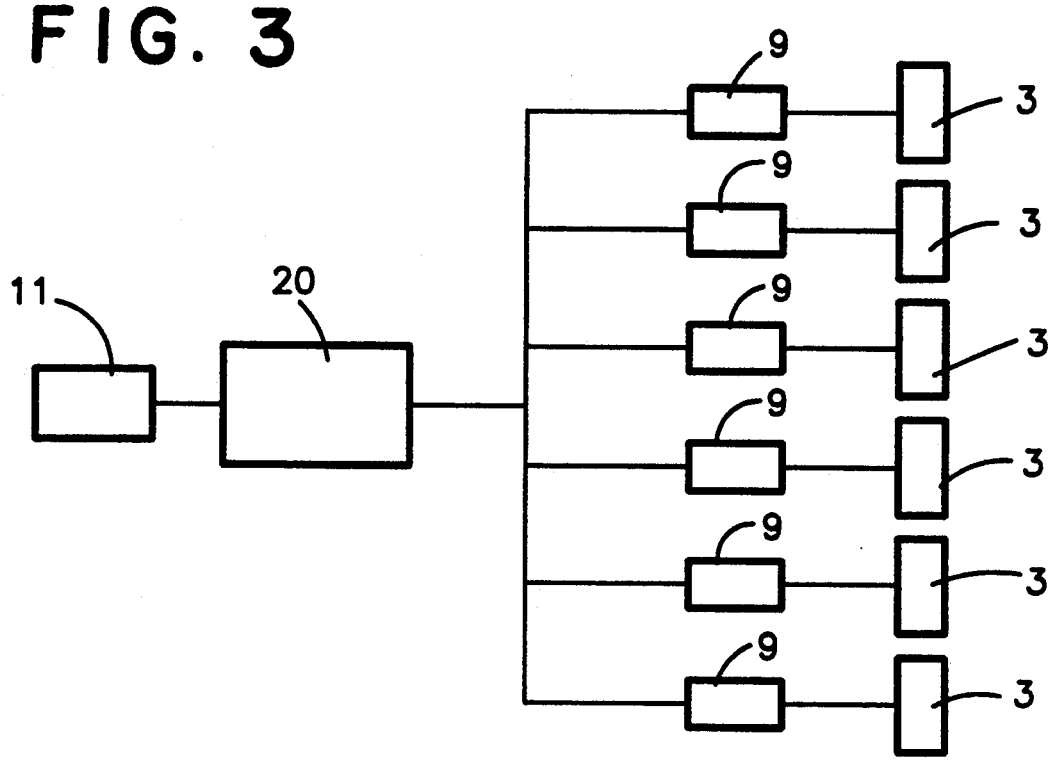
FIG. 3 is a schematic of the computer and drive units for driving the respective connecting elements; and, FIG. 4 is a schematic plan view showing two imaginary circles along which the lower and upper articulating joints of the ceiling suspension are mounted on the first and second platforms, respectively, thereof.

The connecting elements 3 are connected to respective drive units 9 which are driven by a computer 20 as shown schematically in FIG. 3.

The connecting points of the connecting elements 3 are arranged on imaginary circles 16 and 18 on platforms 2 and 4, respectively. The connecting points are arranged next to each other in pairs and the connecting point pairs are displaced one from the other by 120° as shown. The position of the pairs on the platform 2 is displaced with respect to the position of the pairs on platform 4 by 60° along the imaginary circle.

Figure 4:
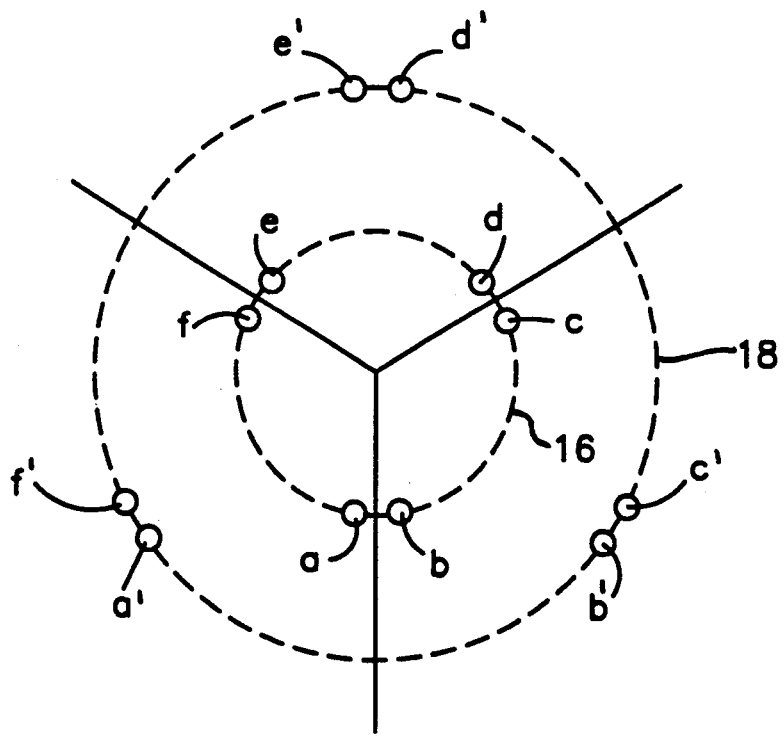

Referring to FIG. 4, six lower articulating joints (a, b, c, d, e, f) connect respective ones of the first ends of the connecting elements 3 to the first platform 2 and six upper articulating joints (a', b', c', d', e', f') connect respective ones of the second ends of the connecting elements 3 to the second platform 4. The lower articulating joints are disposed on the first platform 2 along an imaginary first circle 16 and the upper articulating joints are disposed on the second platform 4 along an imaginary second circle 18. The six lower articulating joints are grouped in three first pairs (a, b), (c, d) and (e, f) with the articulating joints of each first pair being disposed next to each other. Each two first pairs of the lower articulating joints are spaced 120° along the first circle 16. The six upper articulating joints are grouped in three second pairs (b', c'), (d', e') and (f', a') with the articulating joints of each second pair being disposed next to each other. Each two second pairs of the upper articulating joints are spaced 120° along the second circle 18. The first pairs (a, b), (c, d) and (e, f) of lower articulating joints are displaced 60° along the first circle 16 relative to the second pairs (b', c'), (d', e') and (f', a') of the upper articulating joints.

The displacement of the surgical microscope 1 takes place via the respective drives of the connecting elements 3 with the drives being matched one to the other. This movement can be carried out, for example, via a handle 11 which has contacts analog to those of a joystick for controlling the desired movement. The handle 11 is connected to the computer 20 wherein appropriate hardware and software match the drives 9 to provide the desired movement of the extendable connecting elements 3 to facilitate the movement of the lower platform 2.

The displacement in the x, y, and z directions as well as tilting and rotation of the surgical microscope is made possible by the arrangement of the six elements. In this way, all possible degrees of freedom can be controlled and fixed.

Figure 2:
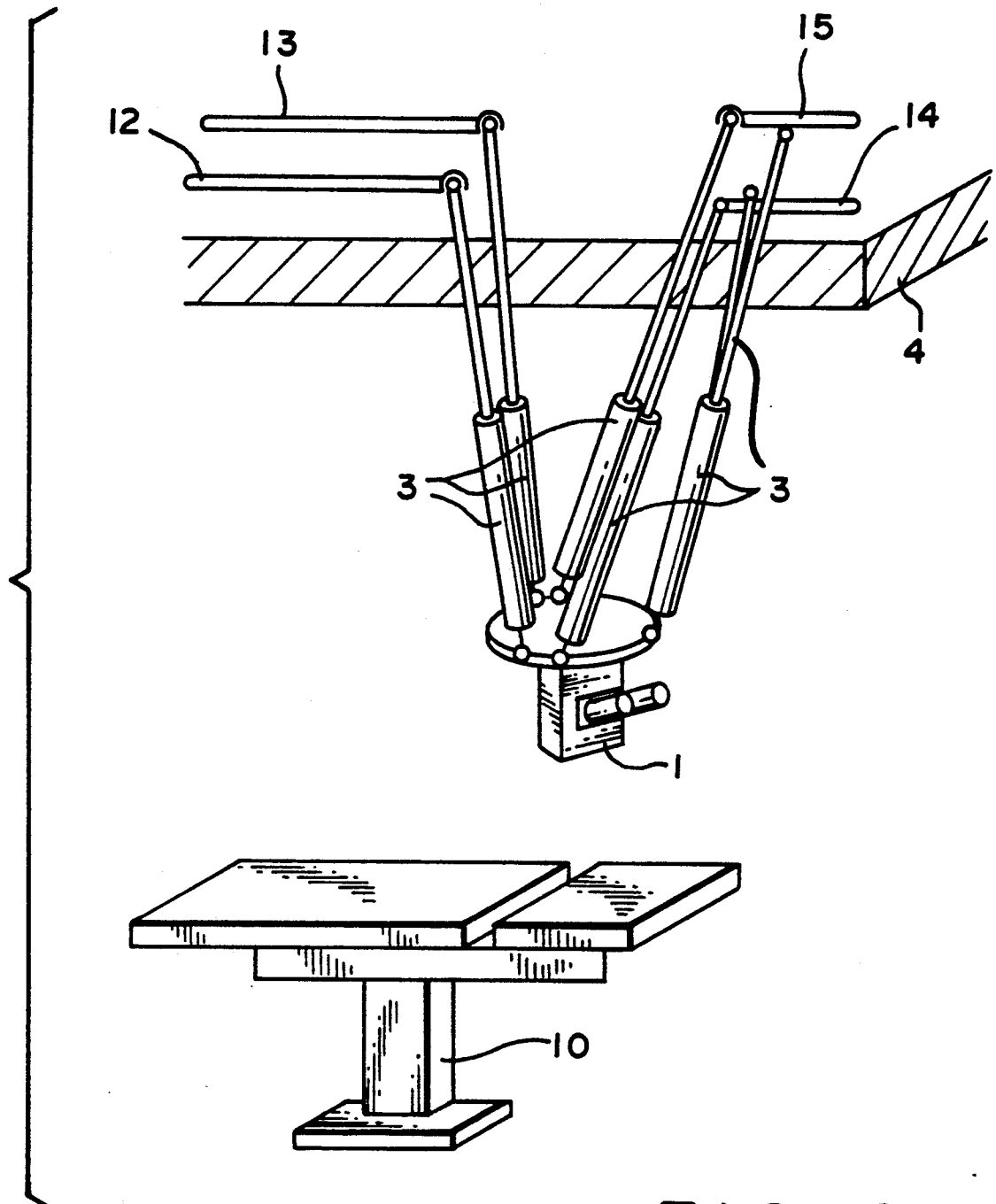
FIG. 2 is a schematic of another embodiment of the ceiling suspension of the invention wherein the surgical microscope can be pivoted out of the operating area.

In the embodiment of FIG. 2, guides 12 to 15 are provided for four of the six ball joints defining the connection to the upper platform. The guides 12 to 15 make it possible to swing the surgical microscope away when the connecting points are unlatched. Two connecting points remain fixed. The length of the connecting elements 3 remains unchanged when swinging the microscope away. This makes it possible for the operator to pivotally return the microscope to the precise same initial position.

Additional advantages are provided by using the platform 2 such as for covering the microscope with a covering hood which is tight with respect to gas and dust since the covering hood is easily attached to the platform. Furthermore, a projection device as well as additional illuminating devices for the area surrounding the operating location can be provided on the platform 2.

It is understood that the foregoing description is that of the preferred embodiments of the invention and that various changes and modifications may be made thereto without departing from the spirit and scope of the invention as defined in the appended claims.

What is claimed is:

1. A three-dimensional adjustable ceiling suspension for a surgical microscope, the ceiling suspension comprising:

a first platform for holding the surgical microscope;

a second platform connected to a ceiling and being disposed above and in spaced relationship to said first platform;

six extendable connecting elements;

each of said connecting elements having first and second ends;

six lower articulating joints for connecting respective ones of the first ends of said connecting elements to said first platform;

six upper articulating joints for connecting respective ones of the second ends of said connecting elements to said second platform;

said lower articulating joints being disposed on said first platform along an imaginary first circle and said upper articulating joints being disposed on said second platform along an imaginary second circle;

said six lower articulating joints being grouped in three first pairs with the articulating joints of each first pair being disposed next to each other;

each two first pairs of said lower articulating joints being spaced 120° along said first circle;

said six upper articulating joints being grouped in three second pairs with the articulating joints of each second pair being disposed next to each other;

each two second pairs of said upper articulating joints being spaced 120° along said second circle;

said first pairs of lower articulating joints being displaced 60° along said first circle relative to said second pairs of said upper articulating joints; and, a plurality of drive units connected to corresponding ones of said extendable connecting elements.

2. The ceiling suspension of claim 1, each of said extendable connecting elements being a hydraulic cylinder and piston unit.

3. The ceiling suspension of claim 1, each of said extendable connecting elements including a spindle drive.

4. The ceiling suspension of claim 1, said second platform having four guide rails provided thereon; the upper articulating joints of a first one of said second pairs being movably mounted in first and second ones of said guide rails; one upper articulating joint of a second one of said second pairs being movably mounted in a third one of said guide rails; and, one upper articulating joint of a third one of said second pairs being movably mounted in a fourth one of said guide rails; and, latching means for latching and unlatching the articulating joints movably mounted in said guide rails in a first position corresponding to the work position of the surgical microscope and in a second position corresponding to the rest position thereof.

* * * * *